(12) United States Patent
Joseph

(10) Patent No.: US 8,993,010 B2
(45) Date of Patent: Mar. 31, 2015

(54) INSECT REPELLENT COMPOUND, MATERIAL AND ANIMAL MASK, AND METHOD FOR MAKING THE SAME

(75) Inventor: Coito Joseph, Gustine, CA (US)

(73) Assignee: Animal Supplies International, Inc., Modesto, CA (US)

( * ) Notice: Subject to any disclaimer, the term of this patent is extended or adjusted under 35 U.S.C. 154(b) by 342 days.

(21) Appl. No.: 12/766,824

(22) Filed: Apr. 23, 2010

(65) Prior Publication Data

US 2011/0104312 A1 May 5, 2011

Related U.S. Application Data

(60) Provisional application No. 61/214,528, filed on Apr. 24, 2009.

(51) Int. Cl.
| | |
|---|---|
| *A61K 36/534* | (2006.01) |
| *D04H 1/00* | (2006.01) |
| *A01K 1/015* | (2006.01) |
| *A01N 25/08* | (2006.01) |
| *A61K 36/48* | (2006.01) |
| *A42B 1/18* | (2006.01) |
| *A61K 36/752* | (2006.01) |
| *A01K 13/00* | (2006.01) |
| *A01N 25/34* | (2006.01) |
| *A01N 65/00* | (2009.01) |
| *A01N 65/36* | (2009.01) |
| *A61D 9/00* | (2006.01) |

(52) U.S. Cl.
CPC ............. *A01K 13/006* (2013.01); *A01K 13/003* (2013.01); *A01N 25/34* (2013.01); *A01N 65/00* (2013.01); *A01N 65/36* (2013.01); *A61D 9/00* (2013.01)
USPC ........... 424/736; 424/747; 424/757; 424/409; 54/80.5; 428/221; 442/361

(58) Field of Classification Search
None
See application file for complete search history.

(56) References Cited

U.S. PATENT DOCUMENTS

| | | | |
|---|---|---|---|
| 2,564,664 A | 8/1951 | Bartlett et al. | |
| 4,662,156 A * | 5/1987 | Oettel | 54/80.2 |
| 5,621,013 A | 4/1997 | Beldock et al. | |
| 6,225,243 B1 * | 5/2001 | Austin | 442/361 |
| 6,524,605 B1 | 2/2003 | Coats et al. | |
| 6,936,269 B2 * | 8/2005 | Robinson | 424/409 |
| 7,144,591 B2 | 12/2006 | Bencsits | |
| 7,243,375 B2 | 7/2007 | Seo | |
| 7,381,431 B2 | 6/2008 | Baker et al. | |
| 2003/0108582 A1 * | 6/2003 | Willis | 424/405 |
| 2005/0112164 A1 | 5/2005 | Lewey | |
| 2006/0257441 A1 | 11/2006 | Komai et al. | |
| 2007/0224232 A1 | 9/2007 | Sherwood | |
| 2008/0175879 A1 | 7/2008 | Feinberg | |
| 2008/0193387 A1 | 8/2008 | De Wolff | |

FOREIGN PATENT DOCUMENTS

| | | |
|---|---|---|
| JP | 200457096 A * | 2/2004 |
| WO | WO2007085856 | 8/2007 |

OTHER PUBLICATIONS

Belen M. Perez Rivera, Plasma-Aided Antimicrobial and Insect Repellant Finishing of Cotton, 2006, 92 pages, USA.
Durvet, FlyRid, DuraMask V, 2009, 5 pages.
Farnam, SuperMask, 2003, 5 pages.
Farnam, SuperMask II, 2003, 5 pages.

* cited by examiner

*Primary Examiner* — Chris R Tate
*Assistant Examiner* — Russell Fiebig

(57) ABSTRACT

An insect repellent compound that includes naturally occurring oil that emits an odor which repels insects is described. The compound is not harmful to animals, to humans or to the environment. The compound may be incorporated into materials such as yarn that is woven to form a mesh. The material may be used for making an animal mask, for screen doors and other applications. A method of making the compound and incorporating it into materials and products is described.

8 Claims, 2 Drawing Sheets

INSECT REPELLENT COMPOUND, MATERIAL AND ANIMAL MASK, AND METHOD FOR MAKING THE SAME

CROSS-REFERENCE TO RELATED APPLICATIONS

The present application claims priority on the basis of the prior-pending provisional application No. 61/214,528 entitled "Insect Repellent Compound, Material and Animal Mask, and Method for Making Same" filed Apr. 24, 2009.

FIELD OF THE INVENTION

The field of the current invention generally relates to insect repellent compounds and materials, and applications therefor including animal masks and other protective gear for animals. The field of the current invention also relates to a method of making the foregoing.

BACKGROUND OF THE INVENTION

Insects, such as mosquitoes and flies, are a common irritation for humans and animals alike. Insects can be especially irritating for horses or other animals having large moist eyes that attract flies and other insects. Besides discomfort, insects may also cause infection or spread disease to such animals by biting the animal or crawling on and around the animal's eyes, or other parts of the animal's body.

For example, insects such as flies may pick up bacteria when landing on other animals, garbage, manure piles or other bacteria laden items. Flies may then spread this bacteria to an animal by biting it or by crawling on or around the animal's eyes or other part of its body. When considering that flies may travel several miles and land many times a day, flies may pick up and transmit a variety of harmful bacteria to a number of animals.

The discomfort and disease spread by such insects may also negatively impact the people who care for such animals. For example, the bites of insects and/or their presence on a horse's eyes may cause a sudden reaction by the horse which could injure someone nearby. And where a person is on the horse, insect bites and/or insects crawling on or around the eyes of a horse can distract the horse and cause sudden movements which could injure the rider.

Different products have been developed to protect horses and other animals from insects. Horse masks, for example, have been developed to physically prevent insects from contacting the eyes or face of a horse. However, those horse masks may be made of heavily woven fabric that may reduce the visibility of the animal wearing them. In addition, they may be cumbersome and uncomfortable for the horse to wear.

Insect repellent creams, ointments or sprays have also been used as chemical repellents to insects from contacting the face or eyes of animals. Oftentimes, these materials comprise synthetic chemicals that are applied directly to a horse near the horse's eyes or to the horse mask.

However, it is undesirable for such repellents, especially those made of synthetic chemicals, to enter an animal's eyes or other area for which the repellent is not intended. This may unfortunately occur, however, because repellent applied near a horse's eyes may still migrate too near or into the eyes, or because sprays may be difficult to direct to a specific area. Furthermore, the protection from such materials may last for only a limited time. Accordingly, repeated application may be required to effectively protect the animal, which may prove burdensome for the person applying the repellent material.

Other existing masks have also comprised an anthelmintic mesh impregnated or otherwise coated with a pesticide or other chemical that resists insects. However, such chemical pesticides may also be harmful to the horse or person caring for the horse, and may also pollute or otherwise harm the environment.

In view of the foregoing, there exists a need for an animal mask that includes an insect repellent compound that provides safety and comfort to the animals wearing them and safety to the humans caring for such animals. There is also a need for such a compound that repels insects for longer periods of time and that is environmentally friendly. There is also a need for an insect repellent compound for other uses such as with window or door screens for houses or other buildings.

SUMMARY OF THE INVENTION

A first aspect of the invention involves a material such as a resin or compound that emits an insect repellent odor and that may be coated on, incorporated into or otherwise applied to an article, such as a mesh or netting, that is used to manufacture protective gear for an animal, such as a mask, blanket or fly mesh, to protect and provide comfort to animals. The repellent material may also be coated on, incorporated into or otherwise applied to other items such as window and door screens to repel insects from houses and other buildings.

In another aspect of the invention, the insect repellent includes a naturally occurring oil that is not harmful to animals, to humans caring for the animals or to the environment. For example, an embodiment of the insect repellent may include a naturally occurring citrus oil that emits an insect repellent odor. Other suitable repellent materials may include odor emitting oils such as mint, fennel, clove, lavender, eucalyptus, citronella, pelargonium, basil, thyme or other naturally occurring ingredients.

Another aspect of the invention involves the ingredients of the insect repellent material. An embodiment suitable for animal masks, blankets or fly mesh, and window or door screens, involves PVC, DINP plasticizer, epoxy soybean oil, additives such as $CaCO_3$, an oil extract such as orange citrus oil, lubricant OPE, an ultraviolet resistant ingredient, antioxidant, auxiliary antioxidant, stabilizer and pigment. Another embodiment may use other ingredients such as epoxy soybean oil or rosin or mint essential oil which may be effective to repel termites.

Another aspect of the invention involves the preparation of the ingredients comprising the resin or compound or other type of repellent material. For example, the ingredients may be mixed in a blender to form a powder. The powder may then be granulated.

Another aspect of the invention involves a method of incorporating the insect repellent resin or compound or other type of repellent material into an article. For example, the resin or compound may be drawn onto a yarn, which yarn is then woven into a mesh fabric for use in animal masks, blankets, fly mesh or other applications. When the yarns are woven together, they may be hot set to fasten the warp and weft yarns together.

In another aspect of the invention, the odor emitting orange citrus or other oil used in the repellent material provides an odor for increased length of time. For example, the resin or compound is preferably resistant to the temperatures associated with manufacturing the product. The product is also preferably packaged to seal in the odor during shipping or shelf life. Accordingly, odor will remain with the product after manufacturing and shipping so that an odor is emitted to repel insects for an increased length of time.

Another aspect of the invention involves an animal mask made of a lower density mesh material impregnated with the resin or compound of the current invention. The lower density mesh is more comfortable for the animal to wear, provides better visibility and ventilation and also decreases manufacturing costs.

Another aspect of the invention involves providing a mask, blanket, fly mesh or other product that includes a naturally occurring, environmentally friendly oil or other material to resist insects. In this manner, the use of pesticides or other chemicals that may harm the environment are avoided.

One embodiment of the invention involves an animal mask for repelling insects, comprising a mesh material that is configured to cover a part of the animal and that includes an insect repellent material. The insect repellent material includes a naturally occurring extract essential oil. The insect repellent material includes a citrus oil. The insect repellent material includes an oil of mint, fennel, clove, lavender, eucalyptus, citronella, pelargonium, basil or thyme. The mesh comprises a plurality of yarns, and the yarns comprise an inner core and an outer coating that includes the insect repellent material. The yarns are hot set. The insect repellent material comprises PVC, a plasticizer, a naturally occurring extract essential oil, an antioxidant and a stabilizer. The animal mask further comprises fleece attached to at least some of the edges of the animal mask. The mask is configured to fit over part of the animal's head including the eyes. The mask is configured to fit over a part of a horse's head including the eyes.

Another embodiment of the invention involves an animal mask for repelling insects, comprising a mesh material that is configured to cover at least a part of the animal's head including the eyes, and that comprises a plurality of yarns; wherein the yarns include an inner core and an outer coating that includes an insect repellent material including a naturally occurring extract essential oil. The naturally occurring extract essential oil is a citrus oil. The naturally occurring extract essential oil is an oil of mint, fennel, clove, lavender, eucalyptus, citronella, pelargonium, basil or thyme. The mask is configured to fit over a part of a horse's head including the eyes.

Another embodiment of the invention involves an insect repellent, comprising PVC; a plasticizer DINP; epoxy soybean oil; a calcium carbonate additive; a naturally occurring extract oil; a lubricant; UV resistant material; an antioxidant; and a stabilizer. The naturally occurring oil is a citrus oil. The naturally occurring oil is an oil of mint, fennel, clove, lavender, eucalyptus, citronella, pelargonium, basil or thyme. The ingredients undergo a mixing cycle for about 9 to about 15 minutes at a temperature of between about 80 degrees C. to about 110 degrees C. The naturally occurring extract oil is added to the mix near the end of the mixing cycle. The mixture is granulated.

Further aspects, objects, and desirable features, and advantages of the invention will be better understood from the following description considered in connection with the accompanying drawings in which various embodiments of the disclosed invention are illustrated by way of example. It is to be expressly understood, however, that the drawings are for the purpose of illustration only and are not intended to limit the invention.

DETAILED DESCRIPTION OF THE PREFERRED EMBODIMENTS

Figure 1:
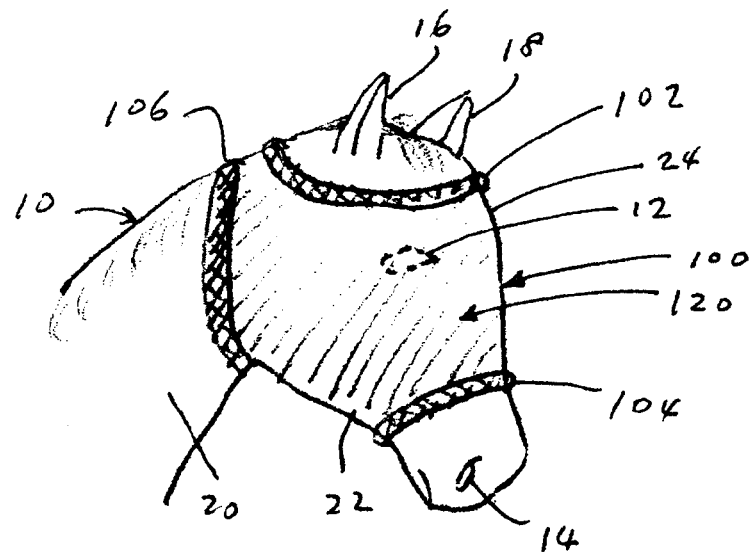
FIG. 1 shows a horse wearing a horse mask comprising a mesh fabric having an insect repellent coating according to an embodiment of the present invention.

Embodiments of the invention will now be described with reference to the figures. To facilitate the description, any reference numeral representing an element in one figure will represent the same element in any other figure.

FIG. 1 shows a horse 10 wearing a mask 100 comprising a mesh fabric 120 according to an embodiment of the current invention. FIG. 1 also shows the horse's eye 12 (shown under the mask 100), nose 14, ears 16, 18, neck 20, jaw 22, and forehead 24. The current invention is not limited to horses but may be used with other animals. The current invention is not limited to animal masks, but may be used with animal blankets that may cover the horse's or other animal's body, fly mesh and other gear.

The horse mask 100 may be tailored from a mesh fabric 120, netting or other suitable material to fit the head of a horse 10 or other animal. The edges of the mask 100 may extend to near the ears 16, 18, nose 14 and neck 20 of the horse 10. The mask 100 of the current invention preferably accommodates animals having different head shapes and sizes, and different spacing between eyes, nose, ears and other parts of its body. To this end, the mask 100 may be adjustable through the use of velcro straps or other fasteners that allow the mask 100 to be tightened or loosened. The mask 100 may also be configured to accommodate a certain type or size of animal.

Fleece edges 102, 104, 106 may be added around the edges of the mask 100 to provide comfort to the animal 10 by avoiding any abrasive edge of the mesh 120 or other material from contacting the animal. To this end, it is preferred that the mask 100 is configured to avoid irritating the animal's eyes or skin, and to also avoid causing hair loss on the animal.

Figure 2:
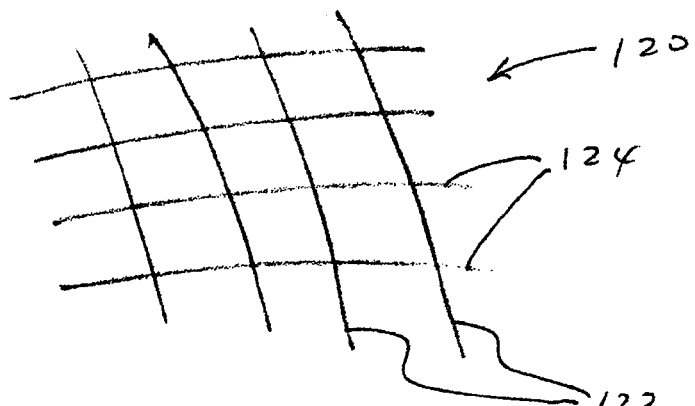
FIG. 2 is an enlarged view of the coated mesh fabric of FIG. 1.

FIG. 2 is an enlarged view of the mesh fabric 120 of FIG. 1. As shown, the mesh fabric 120 is preferably comprised of warp yarns 122 and weft yarns 124 that may be generally perpendicular to each other. In the embodiment shown in FIG. 2, the weft yarn 124 is preferably drawn alternatively over and under the warp yarns 122 to form the mesh fabric 120. Alternative weaving patterns may also be used and the current invention is not limited to the weaving pattern shown in FIG. 2.

Figure 3:
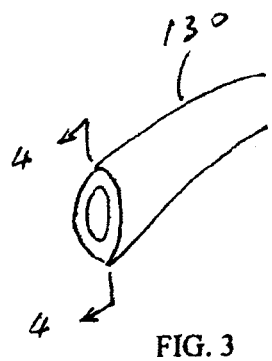
FIG. 3 is an enlarged view of a single piece of yarn from the mesh fabric of FIG. 2.
Figure 4:
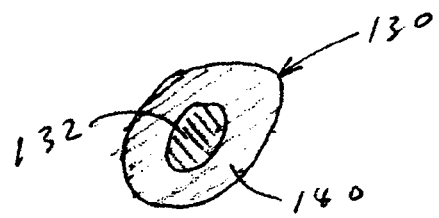
FIG. 4 is a cross-sectional view of a single piece of yarn taken along the plane indicated by 4-4.

FIG. 3 shows an enlarged view of a single fiber or yarn strand 130 taken from the mesh fabric 120 of FIG. 2. FIG. 4 is a cross-sectional view of the single fiber or yarn strand 130 taken along the plane indicated by 4-4.

The fiber or yarn 130 preferably includes an inner core 132 that may be coated by an outer coating 140 that may comprise and/or include the insect repelling material, e.g., resin or compound, of the current invention. In a preferred embodiment, the inner core 132 may comprise polyethylene terephthalate (PET) for its strength and abrasion resistance. Alternatively, the inner core 132 may comprise other natural or synthetic fibers, such as olefin. In one embodiment, the inner core 132 may be 150 D to 1500 D, and have a diameter of about 0.28-0.8 mm. However, the invention is not limited to these characteristics or dimensions. Furthermore, the insect repelling resin or compound may be applied to materials other than yarn and other than in an outer coating configuration. To this end, the insect repellent material may be applied to horse blankets, fly mesh and other protective gear.

The composition and preparation of the insect repelling material, e.g., the resin or compound that may comprise the outer coating 140 or other insect repellent configuration, are now described. In a preferred embodiment, the material may comprise approximately 100 equal parts of polyvinyl chloride (PVC), approximately 38 equal parts of a plasticizer such as diisononyl phthalate (DINP), approximately 5 equal parts of epoxy soybean oil, approximately 10 equal parts of additives such as calcium carbonate ($CaCO_3$), approximately 0.4 equal parts of orange extract essential oil, approximately 0.5 equal parts of lubricant such as OPE, approximately 1.5 equal parts of an ultraviolet (UV) resistant ingredient, approximately 0.3 equal parts of antioxidant, approximately 0.6 equal parts of auxiliary antioxidant and approximately 3 equal parts of stabilizer and a small equal parts of pigment. The current invention is not limited to the components and ratios listed above, but alternatively, the ratios between different components may be varied.

In a preferred embodiment, the PVC may be grade S-65. The plasticizer DINP may be of a type manufactured by ExxonMobil Chemical, and preferably softens the resin or compound. The epoxy soybean oil may be used as a PVC plasticizer and/or to generally increase performance. The $CaCO_3$ additive preferably helps reduce cost and strengthens the PVC. The lubricant may be used to help increase the flexibility of the material including the resin or compound. The UV resistant ingredient may be UV 326 manufactured by Ciba. Preferably, the UV resistant material protects against cracking, fading or other effects of the sun that may be experienced as the product of the current invention is used outdoors. The antioxidant may be Ciba 1010 manufactured by Ciba, and the auxiliary antioxidant may be Ciba 168 manufactured by Ciba. Preferably, these materials may prolong the odor emitting characteristic of the oil. The lubricant may be OPE, i.e., oxidized polyethylene wax. The stabilizer may be a Ca/Zn liquid equalizer, such as Baerostab 9875 manufactured by Baerlocher. The stabilizer may help avoid the PVC breaking down from heat. The pigment may be added so that the resulting resin or compound has a certain color, e.g., black, if desired. The invention is not limited to the foregoing materials and manufacturers, and other alternatives or replacements may be used with the current invention. The foregoing list is for example purposes only.

A preferred embodiment may include orange extract essential oil, or citrus oil, because its odor generally repels insects. As such, it is a preferred ingredient to protect horses or other animals that wear the mask 100, or other protective gear such as a blanket or fly mesh. Orange extract essential oil is also preferred because it is a natural occurring product that does not harm the animal wearing the mask 100, the people who may care for animals or the environment.

Alternatively, other natural essential oils may be used since they also repel insects such as mosquitoes and flies. These may include oils of citrus, mint, fennel, cloves, lavender, eucalyptus, citronella, pelargonium, basil or thyme.

Table 1 is a summary of ingredients for the above-described preferred coating embodiment or other insect repellent material configuration. Again, the ingredients in this table are only for example purposes only and the invention is not limited thereto.

TABLE 1

Summary of Preferred Coating Ingredients

| Component Description | Possible Manufacturer | Grade | Equal Parts |
|---|---|---|---|
| PVC | | S-65 | 100 |
| Plasticizer DINP | ExxonMobil Chemical | | 38 |
| Epoxy Soybean Oil | | | 5 |
| Additives $CaCO_3$ | | | 10 |
| Orange Extract Essential Oil | | | 0.4 |
| Lubricant | | OPE Oxidized Polyethylene Wax | 0.5 |
| UV resistant ingredient | Ciba | UV 326 | 1.5 |
| Antioxidant | Ciba | Ciba 1010 | 0.3 |
| Auxiliary Antioxidant | Ciba | Ciba 168 | 0.6 |
| Stabilizer | Baerlocher | Baerostab 9875 | 3 |
| Pigment | | | small |

The orange extract essential oil, or other natural essential oils, used in connection with the insect repellent material, e.g., outer coating 140 on the fiber or yarn 130, preferably emits an odor over time so that the mask 100, tailored from the mesh fabric 120 comprising the preferred coating, repels insects such as mosquitoes and flies.

The current invention may also be used in other applications where repelling insects is desired. For example, a window or door screen of a farm building or house may comprise a mesh fabric 120 including an orange extract essential oil or other natural essential oils. The insect repellent material may also be applied to other non-mesh type materials. For example, the insect repellent materials may be applied to horse blankets, e.g., coated on blanket fibers or otherwise applied to the blanket.

Some insects are more sensitive to certain odors. For example, termites are repelled by the odor of rosin or mint. Accordingly, in another embodiment of the invention, a carpet mat may include a mesh fabric or yarn with a coating comprising the components shown in Table 2 suitable for repelling termites. Again, the ingredients in this table are only for example purposes only and the invention is not limited thereto.

TABLE 2

Summary of Preferred Coating Ingredients for a Carpet Mat

| Component Description | Possible Manufacturer | Grade | Equal Parts |
|---|---|---|---|
| PVC | | S-65 | 100 |
| Plasticizer DINP | ExxonMobil Chemical | | 36 |
| Epoxy Soybean Oil | | | 5 |
| Additives $CaCO_3$ | | | 50 |
| Rosin Essential Oil | | | 0.4 |
| Lubricant | | OPE Oxidized Polyethylene Wax | 0.5 |
| UV resistant ingredient | Ciba | UV 326 | 1.5 |
| Antioxidant | Ciba | Ciba 1010 | 0.3 |
| Auxiliary Antioxidant | Ciba | Ciba 168 | 0.6 |
| Stabilizer | Baerlocher | Baerostab 9875 | 3 |
| Pigment | | | small |

In another embodiment, a floor cushion may include a mesh fabric or yarn with a coating comprising the components shown in Table 3 for repelling termites.

TABLE 3

Summary of Preferred Coating Ingredients for a Floor Cushion

| Component Description | Possible Manufacturer | Grade | Equal Parts |
|---|---|---|---|
| PVC | Qilu Petrochemical | S1000 | 100 |
| Plasticizer DINP | UPC Group | | 38 |
| Epoxy Soybean Oil | | | 5 |
| Additives CaCO₃ | | | 8 |
| Mint Essential Oil | | | 0.4 |
| Lubricant | | OPE Oxidized Polyethylene Wax | 0.5 |
| UV resistant ingredient | Ciba | UV 531 | 1.5 |
| Antioxidant | Ciba | Ciba 1010 | 0.3 |
| Auxiliary Antioxidant | Ciba | Ciba 168 | 0.6 |
| Stabilizer | Baerlocher | Baerostab 9398 | 4 |
| Pigment | | | small |

It should be noted that the invention is not limited to the specific ingredients and ratios listed above.

Figure 5:
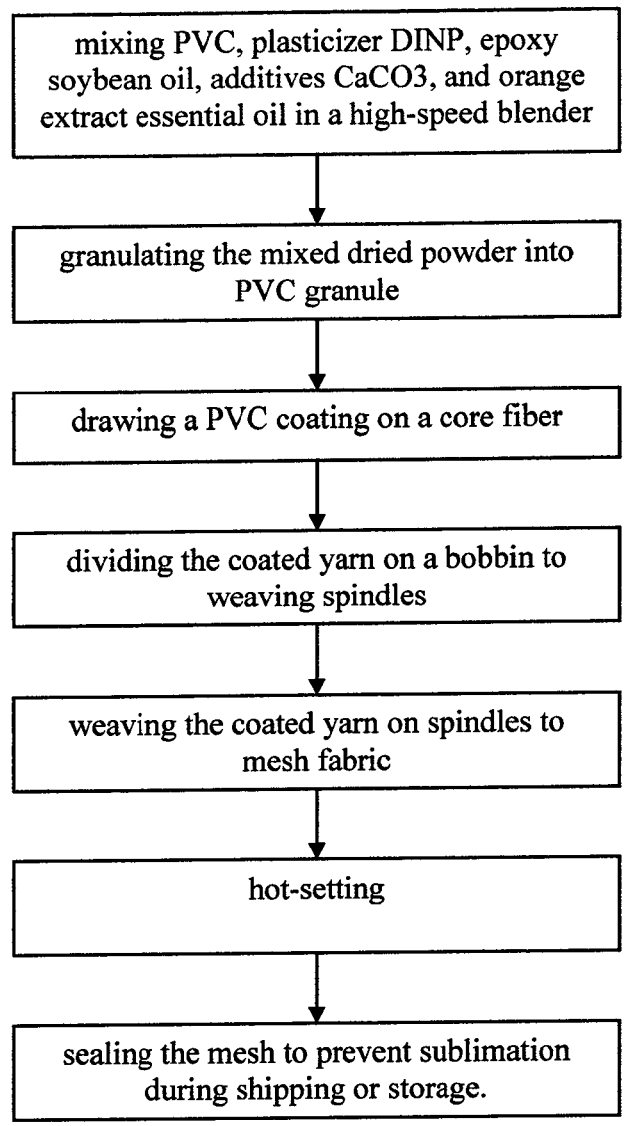
FIG. 5 is a flow chart of a process for making a mesh fabric according to an embodiment of the current invention.

A preferred process for preparing the resin or coating, for coating the fiber or yarn and for preparing the mesh fabric 120 of the current invention is now described with reference to FIG. 5.

In step 210, the components of the resin or coating, such as those in Tables 1, 2 or 3 above, or other suitable ingredients, may be mixed for approximately 9 to 15 minutes at a temperature in the range of about 80° C. to 110° C. until the ingredients are mixed to form a dried powder. It is preferred that a high-speed blender be used and that the ingredients be fully mixed. Other durations and temperatures may also be used. The orange extract essential oil (or other oil) is preferably resistant to high temperatures so that the oil does not lose a significant portion of its odor emitting characteristic during the mixing process. Furthermore, the oil is preferably added to the blender near the end of the mixing step and/or just prior to the next granulating step 220. This preferably helps reduce volatility during mixing and may help the oil retain its odor emitting characteristic. It is preferred that the oil lose less than 20% of its odor emitting characteristic during mixing. This preferably results in the mesh fabric 120 providing an insect repelling odor for an increased time, such as for three to twelve months.

In step 220, the mixed dried powder may be granulated into PVC granule through a PVC granulating extruder. This may occur at a temperature in the range of about 100° C. to 180° C.

In step 230, the PVC coating may be drawn on a core fiber or yarn through a single-screw extruder. In one embodiment, the core fiber or yarn may preferably be 150-1500 D. In one embodiment, the coated fiber or yarn preferably has an outer diameter of 0.28 mm to 0.8 mm, though the dimensions of the core fiber and coated fiber may vary.

In step 240, the coated fibers or yarns may be divided on a bobbin to weaving spindles by a sectional warping machine.

In step 250, the coated fibers or yarns may be weaved on spindles to form a mesh. In one embodiment, the warp density is 8 to 60 yarn/inch and the weft density is 8 to 56 yarn/inch with a rapier loom. The density may vary according to the article being made, e.g., horse masks or horse blankets.

In step 260, the mesh fabric may be hot-set at a temperature in the range of about 100° C. to 190° C. to fasten the warp and weft yarn together to form a mesh fabric. It is again preferred that the orange or other oil is temperature resistant so that it may retain a significant portion of its odor emitting characteristic during the manufacturing process.

In step 270, the mesh fabric or product comprising the mesh is sealed in appropriate packaging to prevent the orange extract essential or other oil integrated in the mesh fabric from sublimation during shipping, storage or shelf life. This preferably contributes to increasing the length of time that the product of the current invention may emit an insect repelling odor.

While various embodiments of a mesh fabric and its respective composition have been presented in the foregoing disclosure, numerous modifications, alterations, alternate embodiments, and alternate materials may be contemplated by those skilled in the art and may be utilized in accomplishing the various aspects of the present invention. For example, the insect repellent material may be applied to other fabrics and materials other than mesh. The insect repellent material may also be applied in manners other than extruding onto yarns. Furthermore, the invention is not limited for use with horses, but may alternatively be used with other domestic or farm animals. Thus, it is to be clearly understood that this description is made only by way of example and not as a limitation on the scope of the invention as claimed below.

What is claimed is:

1. An animal mask for repelling insects, comprising:
a mask formed of a mesh material that includes a core fiber with an outer coating disposed around the core fiber, wherein the outer coating comprises a naturally-occurring essential oil selected from at least one of the following oils: citrus, mint, fennel, clove, lavender, eucalyptus, citronella, pelangonium, basil and thyme; and
wherein the outer coating has greater elasticity than the core fiber.

2. The animal mask of claim 1, wherein the mesh material comprises a plurality of yarns formed from a plurality of core fibers each having an outer coating.

3. The animal mask of claim 2, wherein the yarns are hot set.

4. The animal mask of claim 1, wherein the insect repellent material comprises PVC, a plasticizer, a naturally occurring extract essential oil, an antioxidant and a stabilizer.

5. The animal mask of claim 1, further comprising fleece attached to at least some of the edges of the animal mask.

6. The animal mask of claim 1, wherein the mask is configured to fit over part of an animal's head including the eyes.

7. The animal mask of claim 6, wherein the mask is configured to fit over a part of a horse's head including the eyes.

8. An animal mask for repelling insects, comprising a mask formed of a mesh material that is configured to cover at least a part of the animal's head including the eyes, and comprises yarns, wherein the yarns each includes a core fiber with an outer coating disposed around the core fiber, wherein the outer coating comprises a naturally-occurring essential oil selected from at least one of the following oils: citrus, mint, fennel, clove, lavender, eucalyptus, citronella, pelangonium, basil and thyme; and
wherein the outer coating has greater elasticity than the core fiber.

* * * * *